(12) United States Patent
Abdul-Hafiz

(10) Patent No.: US 7,371,981 B2
(45) Date of Patent: May 13, 2008

(54) CONNECTOR SWITCH

(75) Inventor: Yassir Abdul-Hafiz, Lake Forest, CA (US)

(73) Assignee: Masimo Corporation, Irvine, CA (US)

( * ) Notice: Subject to any disclaimer, the term of this patent is extended or adjusted under 35 U.S.C. 154(b) by 131 days.

(21) Appl. No.: 11/062,169

(22) Filed: Feb. 18, 2005

(65) Prior Publication Data

US 2005/0187440 A1    Aug. 25, 2005

Related U.S. Application Data

(60) Provisional application No. 60/546,531, filed on Feb. 20, 2004.

(51) Int. Cl.
H01R 33/96 (2006.01)
(52) U.S. Cl. .................. 200/51 R; 200/51.09; 439/188
(58) Field of Classification Search ............. 200/43.01, 200/43.04, 43.05, 51 R, 51.05, 51.06, 51.08, 200/51.09, 51.1, 51.11, 51.12, 51.13; 439/188, 439/352, 76.1
See application file for complete search history.

(56) References Cited

U.S. PATENT DOCUMENTS

| | | | |
|---|---|---|---|
| 3,391,262 A * | 7/1968 | Twitchell, Jr. ........... 200/51.02 |
| 4,960,128 A | 10/1990 | Gordon et al. |
| 5,163,438 A | 11/1992 | Gordon et al. |
| 5,337,744 A | 8/1994 | Branigan |
| 5,431,170 A | 7/1995 | Mathews |
| 5,452,717 A | 9/1995 | Branigan et al. |
| 5,482,036 A | 1/1996 | Diab et al. |
| 5,490,505 A | 2/1996 | Diab et al. |
| 5,494,043 A | 2/1996 | O'Sullivan et al. |
| 5,533,511 A | 7/1996 | Kaspari et al. |
| 5,590,649 A | 1/1997 | Caro et al. |
| 5,632,272 A | 5/1997 | Diab et al. |
| 5,638,816 A | 6/1997 | Kiani-Azarbayjany et al. |
| 5,638,818 A | 6/1997 | Diab et al. |
| 5,645,440 A | 7/1997 | Tobler et al. |
| 5,685,299 A | 11/1997 | Diab et al. |
| D393,830 S | 4/1998 | Tobler et al. |
| 5,741,151 A * | 4/1998 | Youngers ..................... 439/489 |
| 5,743,262 A | 4/1998 | Lepper, Jr. et al. |
| 5,758,644 A | 6/1998 | Diab et al. |
| 5,760,910 A | 6/1998 | Lepper, Jr. et al. |
| 5,769,785 A | 6/1998 | Diab et al. |
| 5,782,757 A | 7/1998 | Diab et al. |
| 5,785,659 A | 7/1998 | Caro et al. |
| 5,791,347 A | 8/1998 | Flaherty et al. |
| 5,810,734 A | 9/1998 | Caro et al. |
| 5,823,950 A | 10/1998 | Diab et al. |
| 5,830,131 A | 11/1998 | Caro et al. |
| 5,833,618 A | 11/1998 | Caro et al. |
| 5,860,919 A | 1/1999 | Kiani-Azarbayjany et al. |
| 5,890,929 A | 4/1999 | Mills et al. |

(Continued)

Primary Examiner—Michael A Friedhofer
(74) Attorney, Agent, or Firm—Knobbe, Martens, Olson & Bear, LLP

(57) ABSTRACT

An interconnection between a sensor and a monitor has a cable, an information element and a switch. The cable has conductors providing electrical communication between a sensor connector and a monitor connector. The information element is readable by the monitor and mounted in the sensor connector, the monitor connector or the cable. A switch is mounted in the sensor connector and is responsive to the sensor connecting to and disconnecting from the sensor connector so as to alter the readability of said information element.

12 Claims, 16 Drawing Sheets

U.S. PATENT DOCUMENTS

| | | | |
|---|---|---|---|
| 5,904,654 | A | 5/1999 | Wohltmann et al. |
| 5,919,134 | A | 7/1999 | Diab |
| 5,928,020 | A * | 7/1999 | Bishop et al. .............. 439/188 |
| 5,934,925 | A | 8/1999 | Tobler et al. |
| 5,940,182 | A | 8/1999 | Lepper, Jr. et al. |
| 5,995,855 | A | 11/1999 | Kiani et al. |
| 5,997,343 | A | 12/1999 | Mills et al. |
| 6,002,952 | A | 12/1999 | Diab et al. |
| 6,011,986 | A | 1/2000 | Diab et al. |
| 6,027,452 | A | 2/2000 | Flaherty et al. |
| 6,036,642 | A | 3/2000 | Diab et al. |
| 6,045,509 | A | 4/2000 | Caro et al. |
| 6,056,590 | A * | 5/2000 | Takahashi et al. .......... 439/489 |
| 6,058,444 | A * | 5/2000 | Johnson ...................... 439/188 |
| 6,067,462 | A | 5/2000 | Diab et al. |
| 6,081,735 | A | 6/2000 | Diab et al. |
| 6,088,607 | A | 7/2000 | Diab et al. |
| 6,110,522 | A | 8/2000 | Lepper, Jr. et al. |
| 6,151,516 | A | 11/2000 | Kiani-Azarbayjany et al. |
| 6,152,754 | A | 11/2000 | Gerhardt et al. |
| 6,157,850 | A | 12/2000 | Diab et al. |
| 6,165,005 | A | 12/2000 | Mills et al. |
| 6,184,521 | B1 | 2/2001 | Coffin, IV et al. |
| 6,206,830 | B1 | 3/2001 | Diab et al. |
| 6,229,856 | B1 | 5/2001 | Diab et al. |
| 6,236,872 | B1 | 5/2001 | Diab et al. |
| 6,256,523 | B1 | 7/2001 | Diab et al. |
| 6,263,222 | B1 | 7/2001 | Diab et al. |
| 6,278,522 | B1 | 8/2001 | Lepper, Jr. et al. |
| 6,280,213 | B1 | 8/2001 | Tobler et al. |
| 6,285,896 | B1 | 9/2001 | Tobler et al. |
| 6,334,065 | B1 | 12/2001 | Al-Ali et al. |
| 6,349,228 | B1 | 2/2002 | Kiani et al. |
| 6,360,114 | B1 | 3/2002 | Diab et al. |
| 6,371,921 | B1 | 4/2002 | Caro et al. |
| 6,377,829 | B1 | 4/2002 | Al-Ali |
| 6,388,240 | B2 | 5/2002 | Schulz et al. |
| 6,397,091 | B2 | 5/2002 | Diab et al. |
| 6,430,525 | B1 | 8/2002 | Weber et al. |
| 6,463,311 | B1 | 10/2002 | Diab |
| 6,470,199 | B1 | 10/2002 | Kopotic et al. |
| 6,501,975 | B2 | 12/2002 | Diab et al. |
| 6,515,273 | B2 | 2/2003 | Al-Ali |
| 6,525,386 | B1 | 2/2003 | Mills et al. |
| 6,526,300 | B1 | 2/2003 | Kiani et al. |
| 6,541,756 | B2 | 4/2003 | Schulz et al. |
| 6,542,764 | B1 | 4/2003 | Al-Ali et al. |
| 6,566,767 | B1 * | 5/2003 | Tardo ....................... 200/51.03 |
| 6,580,086 | B1 | 6/2003 | Schulz et al. |
| 6,584,336 | B1 | 6/2003 | Ali et al. |
| 6,597,933 | B2 | 7/2003 | Kiani et al. |
| 6,606,511 | B1 | 8/2003 | Ali et al. |
| 6,632,181 | B2 | 10/2003 | Flaherty et al. |
| 6,640,116 | B2 | 10/2003 | Diab |
| 6,643,530 | B2 | 11/2003 | Diab et al. |
| 6,650,917 | B2 | 11/2003 | Diab et al. |
| 6,654,624 | B2 | 11/2003 | Diab et al. |
| 6,658,276 | B2 | 12/2003 | Diab et al. |
| 6,671,531 | B2 | 12/2003 | Al-Ali et al. |
| 6,678,543 | B2 | 1/2004 | Diab et al. |
| 6,684,090 | B2 | 1/2004 | Ali et al. |
| 6,697,656 | B1 | 2/2004 | Al-Ali |
| 6,697,658 | B2 | 2/2004 | Al-Ali |
| RE38,476 | E | 3/2004 | Diab et al. |
| 6,699,194 | B1 | 3/2004 | Diab et al. |
| 6,714,804 | B2 | 3/2004 | Al-Ali et al. |
| RE38,492 | E | 4/2004 | Diab et al. |
| 6,725,075 | B2 | 4/2004 | Al-Ali |
| 6,745,060 | B2 | 6/2004 | Diab et al. |
| 6,760,607 | B2 | 7/2004 | Al-Ali |
| 6,770,028 | B1 | 8/2004 | Ali et al. |
| 6,771,994 | B2 | 8/2004 | Kiani et al. |
| 6,792,300 | B1 | 9/2004 | Diab et al. |
| 6,813,511 | B2 | 11/2004 | Diab et al. |
| 6,816,741 | B2 | 11/2004 | Diab |
| 6,822,564 | B2 | 11/2004 | Al-Ali |
| 6,826,419 | B2 | 11/2004 | Diab et al. |
| 6,830,711 | B2 | 12/2004 | Mills et al. |
| 6,850,787 | B2 | 2/2005 | Weber et al. |
| 6,850,788 | B2 | 2/2005 | Al-Ali |
| 6,852,083 | B2 | 2/2005 | Caro et al. |
| 6,971,895 | B2 * | 12/2005 | Sago et al. .................. 439/188 |
| 6,986,686 | B2 * | 1/2006 | Shibata et al. .............. 439/650 |

\* cited by examiner

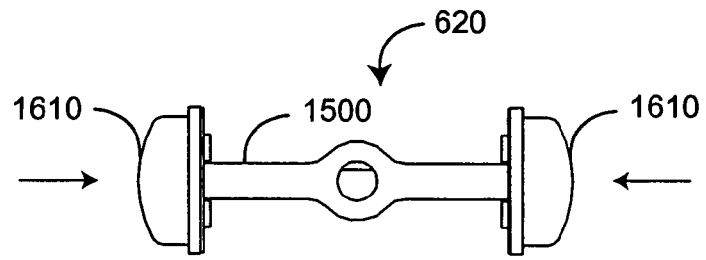
FIG. 7A
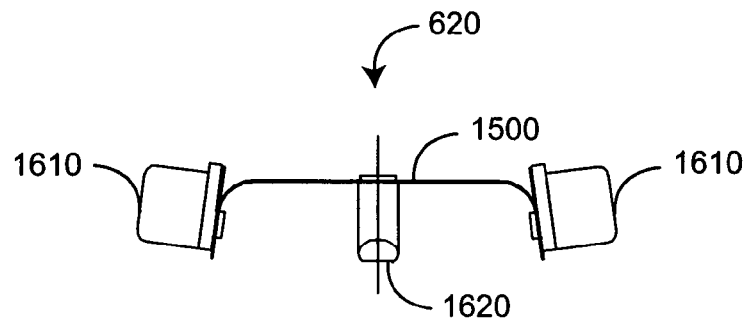
FIG. 7B
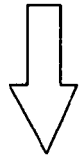
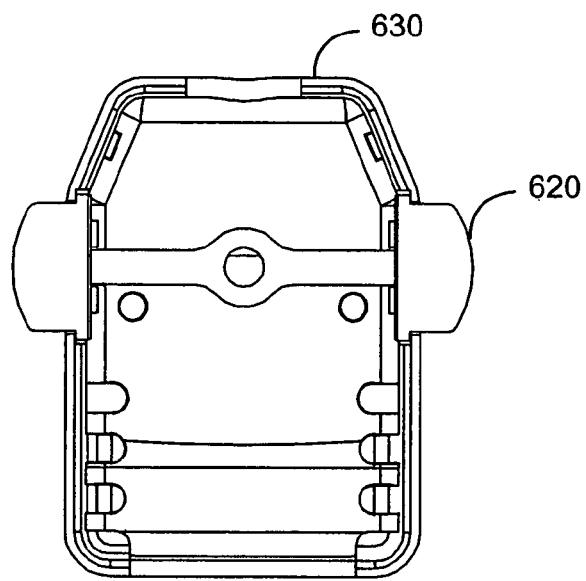
FIG. 7C

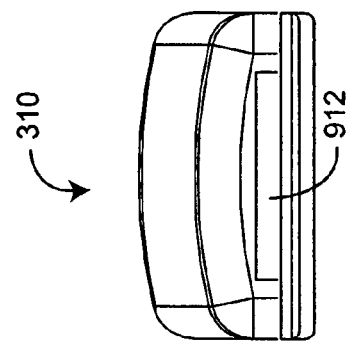
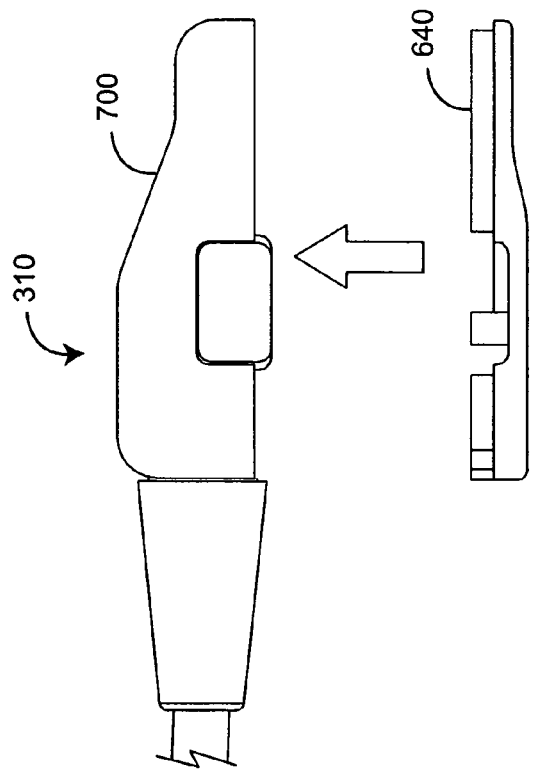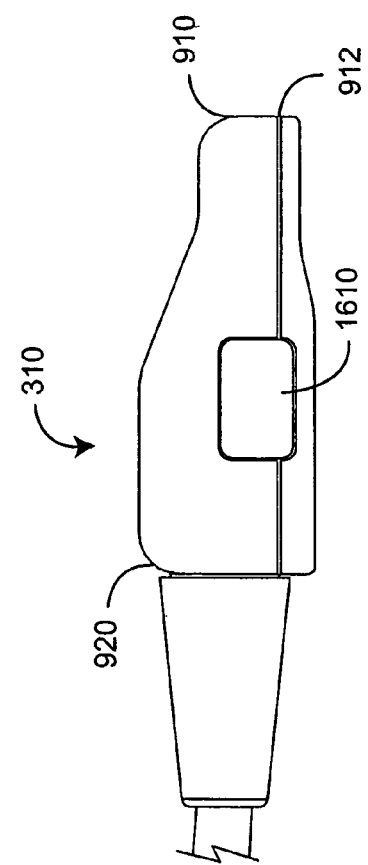

DETAIL A-A

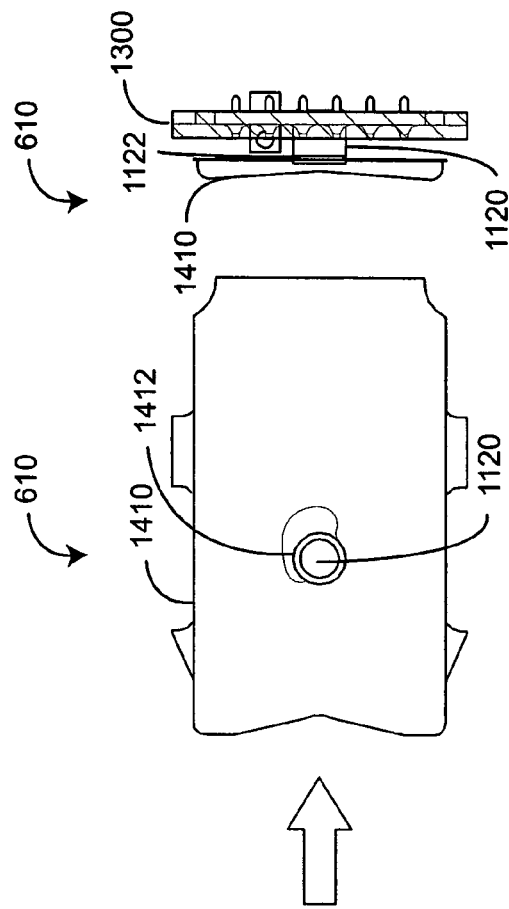
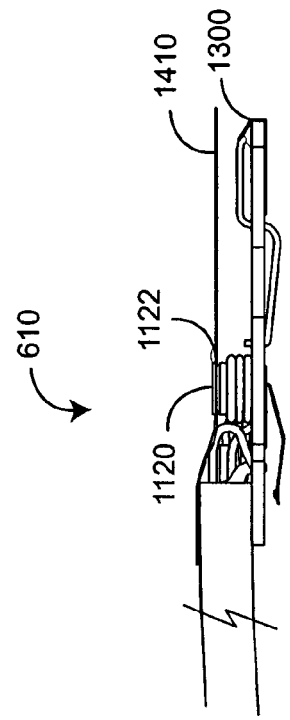
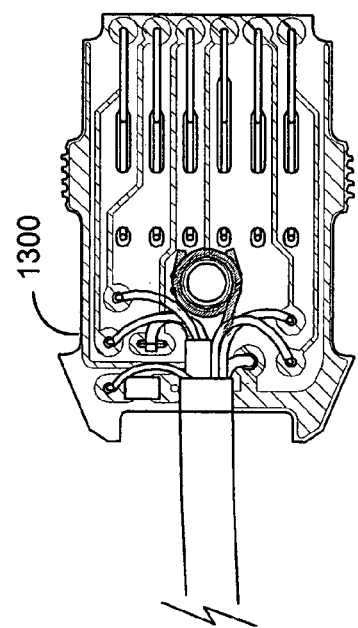
FIG. 14A
FIG. 14B
FIG. 14C
FIG. 13C

CONNECTOR SWITCH

CROSS-REFERENCE TO RELATED APPLICATIONS

This application relates to and claims the benefit of prior U.S. Provisional Application No. 60/546,531 entitled Connector Switch, filed Feb. 20, 2004 and incorporated by reference herein.

BACKGROUND OF THE INVENTION

Pulse oximetry is a widely accepted noninvasive procedure for measuring arterial oxygen saturation, which provides early detection of hypoxia. FIG. 1 illustrates a pulse oximetry system 100 having a sensor 110 applied to a patient, a monitor 120, and a patient cable 130 connecting the sensor 110 and the monitor 120. The sensor 110 has emitters and a detector, which are attached to a tissue site, such as a finger as shown. The patient cable 130 transmits an emitter drive signal from the monitor 120 to the sensor 110 and a resulting detector signal from the sensor 110 to the monitor 120. The monitor 120 processes the detector signal to provide a numerical readout of oxygen saturation and pulse rate.

FIGS. 2A-B illustrate a pulse oximetry sensor 110. As shown in FIG. 2A, the sensor 110 has an adhesive wrap 205 that positions emitters 250 (not visible) proximate, for example, a finger nail and a detector 260 (not visible) proximate a finger pad. A sensor plug 200 inserts into a sensor connector 135 (FIG. 1) so that plug contacts 201 are in electrical communications with the monitor 120 (FIG. 1) via the patient cable 130 (FIG. 1).

As shown in FIG. 2B, a pulse oximetry sensor 110 has both red and infrared light emitting diode (LED) emitters 210, 220 and a photodiode detector 230. LED pinouts 250 on the plug contacts 201 (FIG. 2A) connect the LEDs 210, 220 to the monitor 120 (FIG. 1). Detector pinouts 260 on the plug contacts 201 (FIG. 2A) connect the photodiode 230 to the monitor 120 (FIG. 1). The sensor 110 may also have an information element 240, such as a resistor. The information element 240 may have various uses, such as an indicator of sensor type, depending on the manufacturer. A pulse oximetry sensor is described in U.S. Pat. No. 6,256,523 entitled Low Noise Optical Probes; a pulse oximetry monitor is described in U.S. Pat. No. 6,826,419 entitled Signal Processing Apparatus And Method; and an information element is described in U.S. Pat. No. 5,758,644 entitled Manual and Automatic Probe Calibration, all of which are assigned to Masimo Corporation, Irvine, Calif. and incorporated by reference herein.

SUMMARY OF THE INVENTION

A patient cable can be an adapter cable. That is, it can function to physically and electrically adapt a sensor to an otherwise incompatible monitor. For example, some monitors are configured to read a sensor information element. An adapter cable for a sensor that does not have an information element can incorporate that element in the adapter cable itself, such as within one of the adapter cable connectors. In some circumstances, however, removing the sensor from such an adapter cable can result in a monitor status message indicating a malfunctioning sensor rather than a disconnected sensor. This arises because the monitor is able to read the information element but is unable to receive a detector signal. A connector switch, however, advantageously electrically disconnects the information element from the monitor when the sensor is disconnected from the adapter cable. In that manner, the monitor will detect the absence of both a sensor and an information element and display a correct status message accordingly.

One aspect of a connector switch is an interconnection between a sensor and a monitor having a cable, an information element and a switch. The cable has conductors providing electrical communication between a sensor connector and a monitor connector. The information element is readable by the monitor and mounted in the sensor connector, the monitor connector or the cable. A switch is mounted in the sensor connector and is responsive to the sensor connecting to and disconnecting from the sensor connector so as to alter the readability of said information element.

Another aspect of a connector switch is an interconnection method that provides a cable configured to communicate drive signals from a physiological parameter monitor to a sensor and physiological signals from the sensor to the monitor. An information element is associated with the cable, where the information element is capable of conveying information regarding the sensor to the monitor. A switch is actuated in response to the sensor connecting and disconnecting to the cable so as to render the information element readable and unreadable by the monitor, respectively.

A further aspect of a connector switch is a sensor-monitor interconnection comprising a cable adapted to communicate signals between a physiological sensor and a physiological parameter monitor. An information element is capable of conveying information regarding the sensor to the monitor. A switch is associated with the cable and responsive to the physiological sensor connecting to and disconnecting from the cable so as to enable and disable the reading of the information element by the monitor.

BRIEF DESCRIPTION OF THE DRAWINGS

FIGS. 7A-C are bottom and side views of a spring assembly and a bottom view of a partial top shell assembly;

FIGS. 9A-C are exploded side, assembled side and assembled front views of a sensor connector;

FIGS. 13A-C are bottom, side and top views of a taped PCB assembly;

FIGS. 14A-C are top, front, and side views of a shielded PCB assembly;

DETAILED DESCRIPTION OF THE PREFERRED EMBODIMENTS

Figure 3:
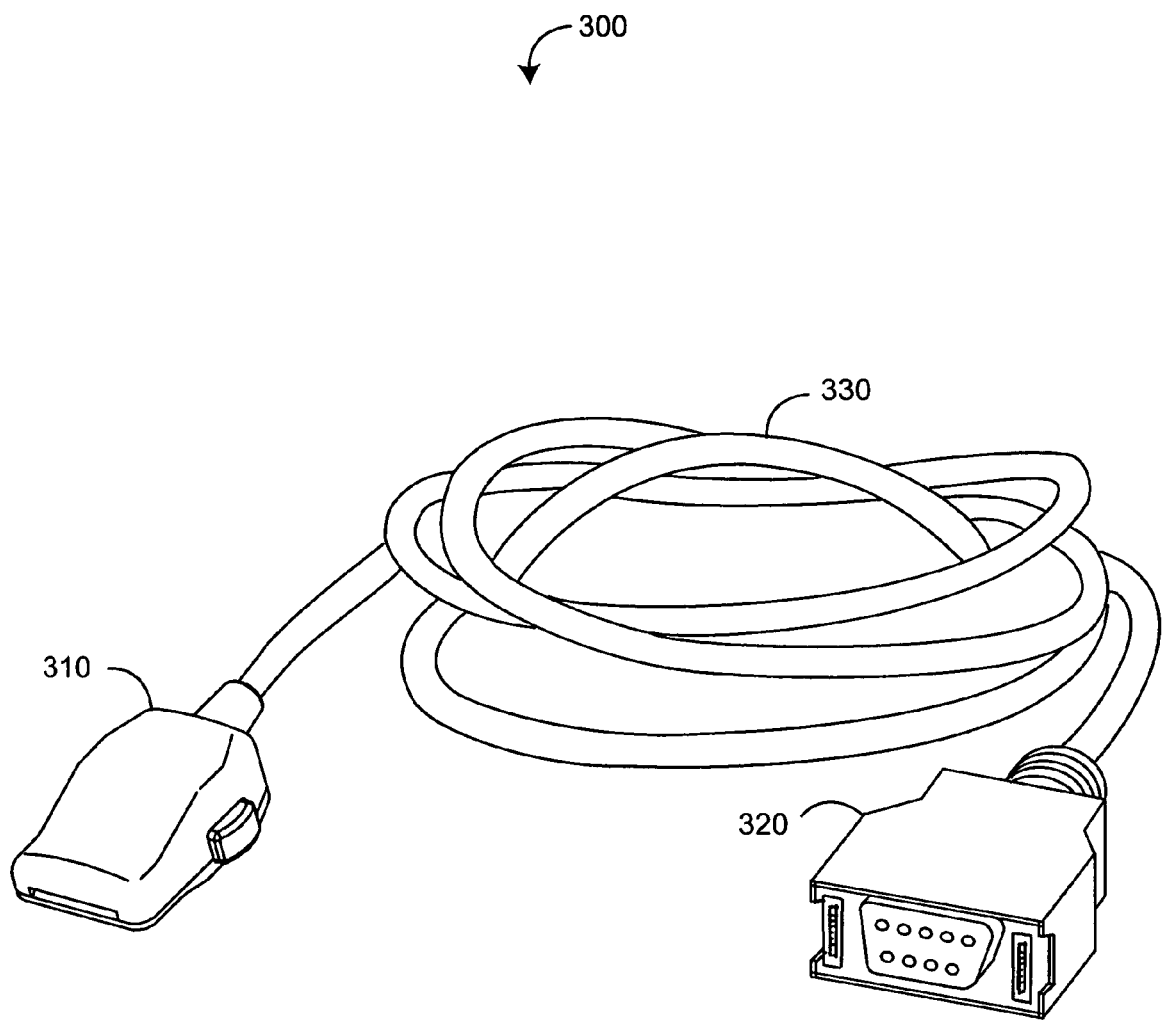
FIG. 3 is a perspective view of a patient cable.
Figure 4:
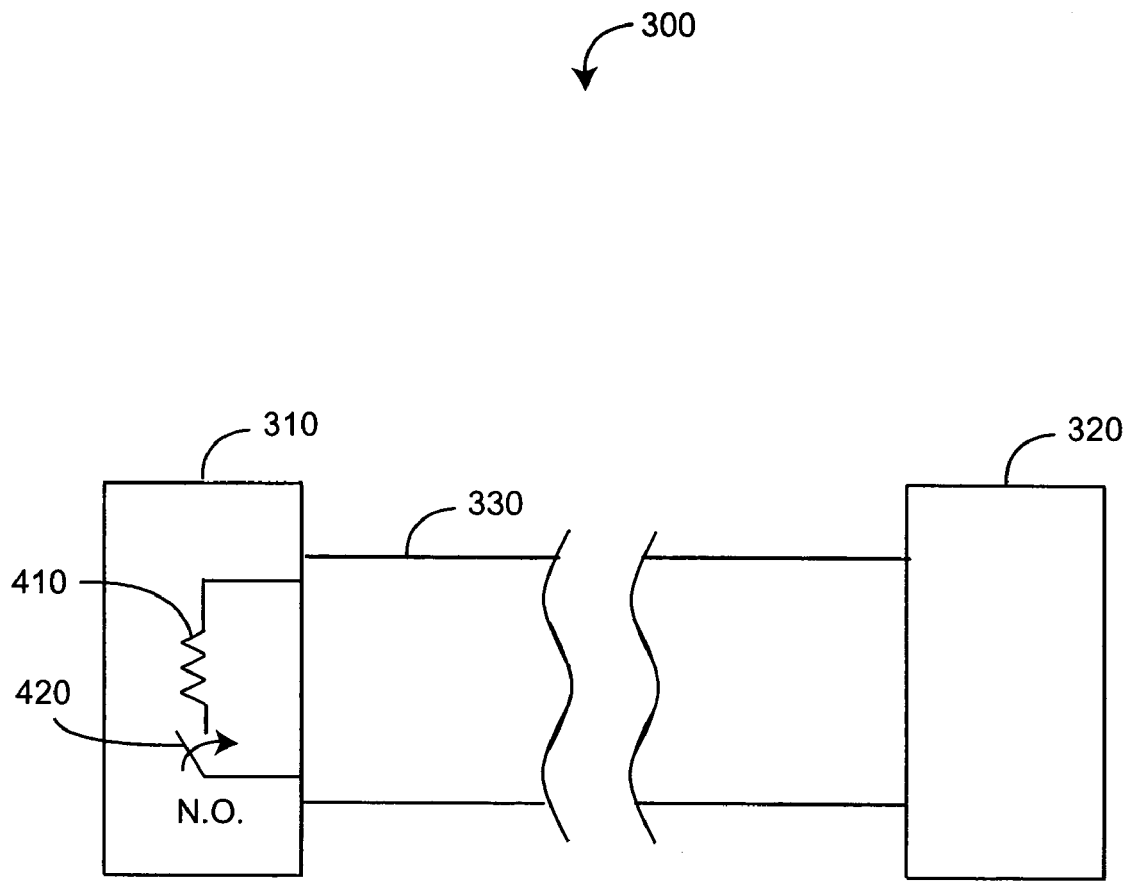
FIG. 4 is a schematic diagram of a patient cable having a connector switch.

FIGS. 3-4 illustrate an adapter patient cable 300 having a sensor connector 310 and a monitor connector 320 physically and electrically connected by a cable 330. The sensor connector 310 has a resistor 410 (FIG. 4) and a normally open (N.O.) switch 420 (FIG. 4) in series with the resistor 410. The resistor 410 functions as a sensor information element, as described above. The switch 420 is responsive to a sensor being attached or removed from the sensor connector 310, as described below. Utilizing the switch 420 to connect and disconnect the resistor advantageously allows a connected monitor to indicate accurate status information regarding a sensor.

In particular, when a sensor is attached to the sensor connector 310, the switch 420 moves to a closed position 522 (FIG. 5B) connecting the resistor 410 to the monitor so that the monitor is able to read the resistor 410. When a sensor is removed from the sensor connector 310, the switch 420 returns to an open position 521 (FIG. 5A) disconnecting the resistor 410 from the monitor so that the monitor is unable to read the resistor 410. As such, the monitor is able to unambiguously detect when a sensor is attached or removed from the sensor connector 310 and, accordingly, the monitor indicates a removed sensor rather than a malfunctioning sensor.

Figure 5A:
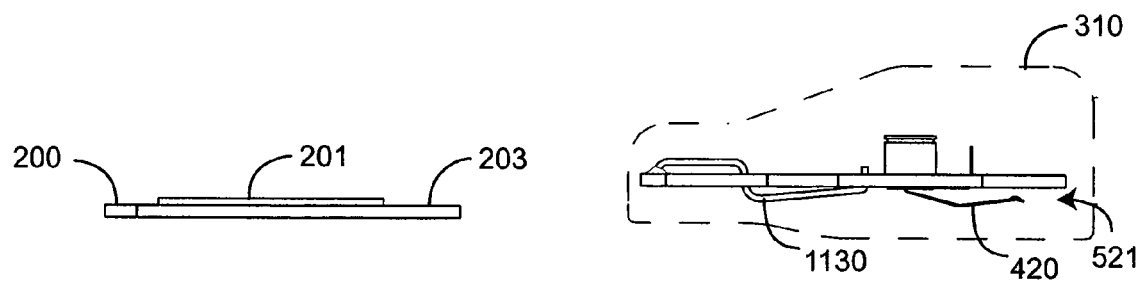
FIGS. 5A-B are side views of unattached and attached sensor and patient cable connectors.
Figure 5B:
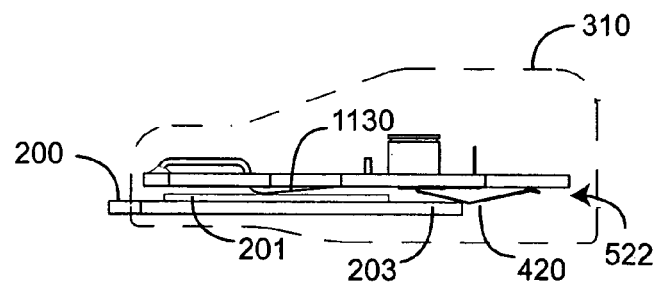

FIGS. 5A-B illustrate the mechanical details of inserting and removing a sensor plug 200 into the sensor connector 310. In particular, when the plug 200 is inserted, plug contacts 201 electrically connect with the sensor connector contacts 1030, and the tab 203 presses the switch 420 to a closed position 522. When the plug 200 is removed, the tab 203 releases the switch 420, which returns to its normally open position 521.

Figure 6B:
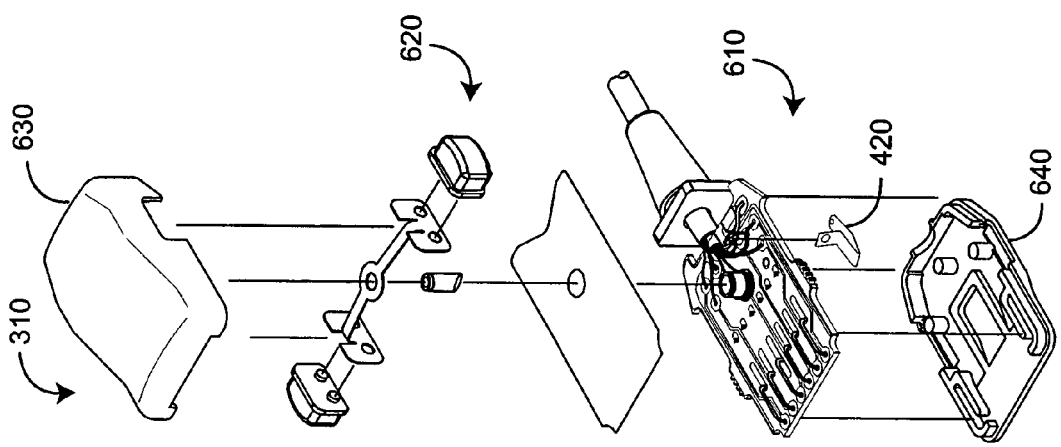
FIGS. 6A-B are exploded bottom and top perspective views of a sensor connector.
Figure 6A:
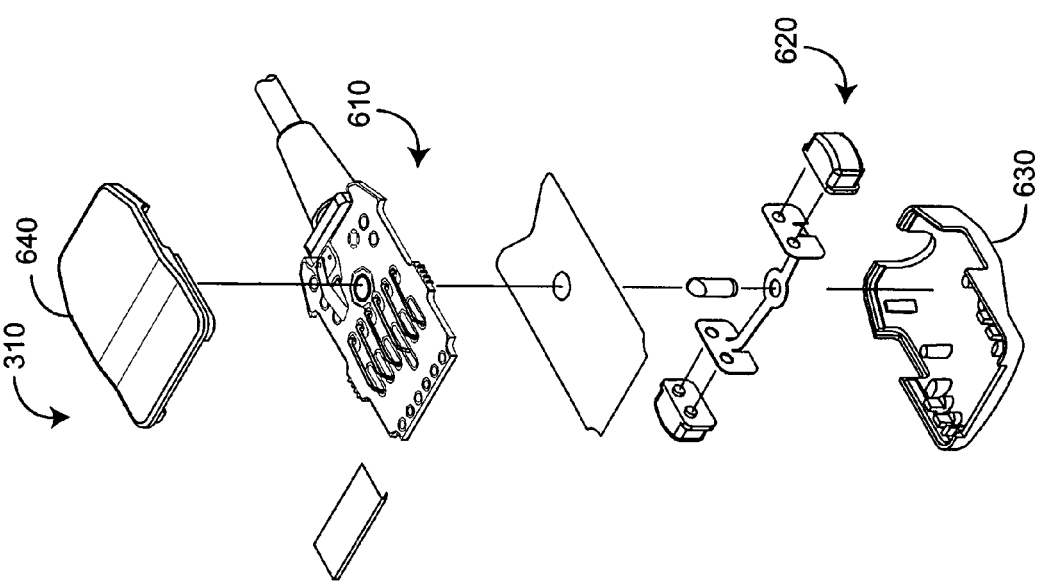
Figure 15A:
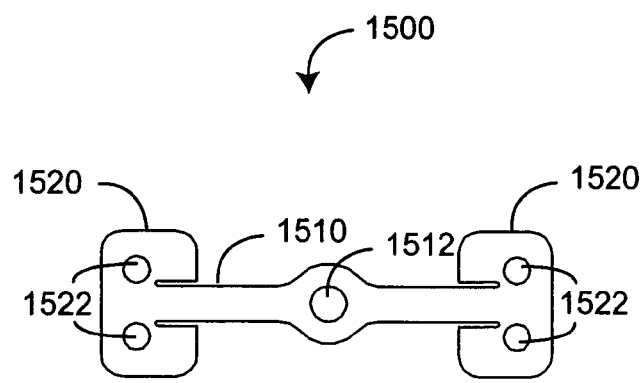
FIGS. 15A-D are unfolded top, top, front, and side views of a connector spring.
Figure 15B:
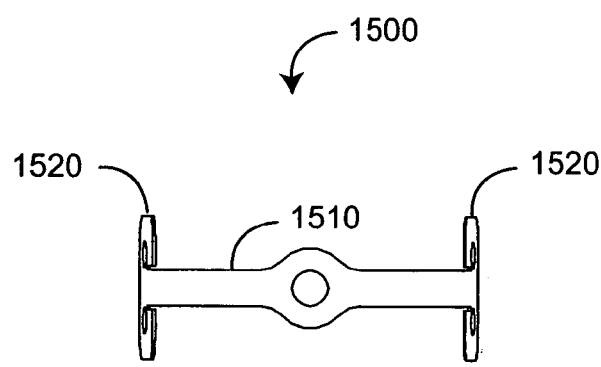
Figures 15C, 15D:
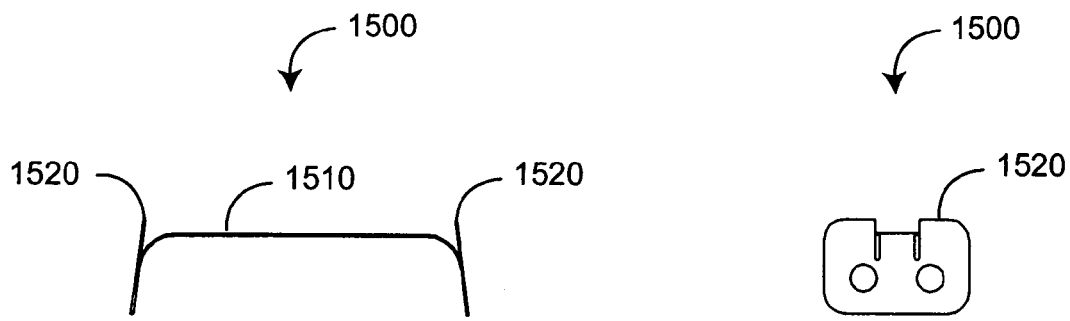

FIGS. 6A-B illustrate a sensor connector 310 having a cable assembly 610, a spring assembly 620, a top shell 630 and a bottom shell 640. Construction of the sensor connector 310 is illustrated in detail with respect to FIGS. 7-9. Construction of the cable assembly 610 is illustrated in detail with respect to FIGS. 10-14. Construction of the spring assembly 620 is illustrated in detail with respect to FIGS. 15-16.

Sensor Connector Construction

Figure 8B:
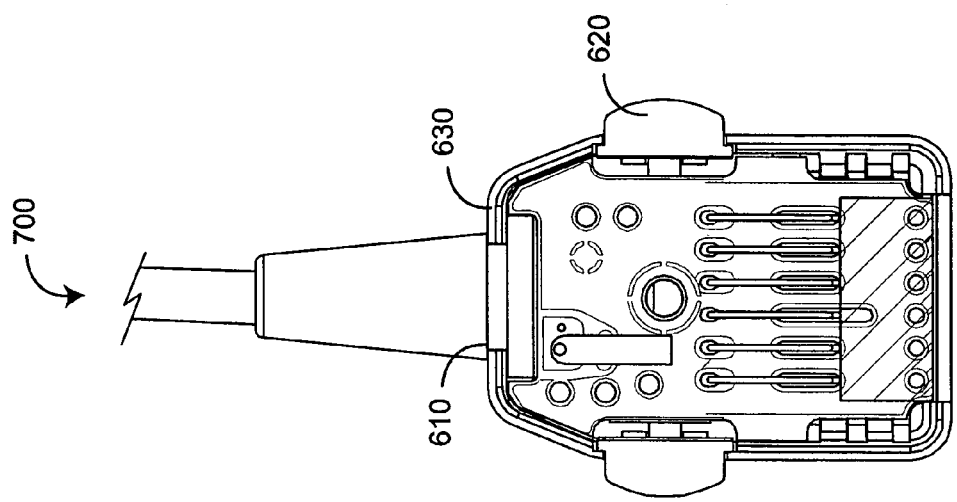
FIGS. 8A-B are bottom views of a printed circuit board (PCB) and a top shell assembly.
Figure 8A:
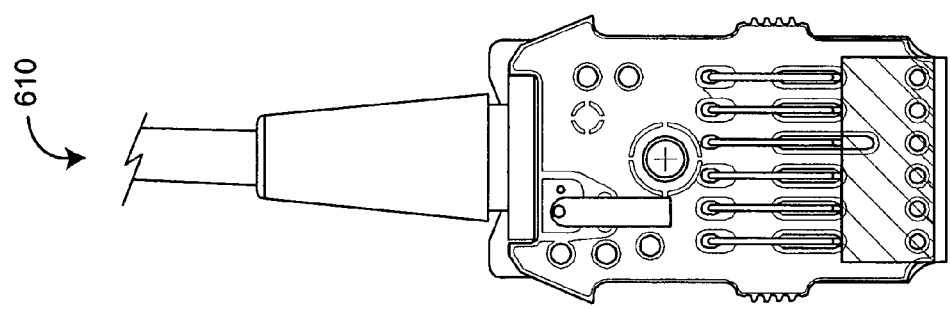

FIGS. 9A-C illustrate a sensor connector 310 having a top shell assembly 700 and a bottom shell 640. FIGS. 8A-B illustrate the top shell assembly 700 having a cable assembly 610, a spring assembly 620 and a top shell 630. FIGS. 7A-B illustrate the spring assembly 620 including a spring 1500, a latch 1620 and buttons 1610 so as to secure and release the tab 203 (FIGS. 5A-B) of a sensor plug 200 (FIGS. 5A-B). FIG. 7C shows the spring assembly 620 is inserted into the top shell 630 As shown in FIGS. 8A-B, the cable assembly 610 is inserted into the top shell 630 over the spring assembly 620. As shown in FIGS. 9A-C, the top shell assembly 700 is attached to the bottom shell 640. In one embodiment, the bottom shell 640 is ultrasonically welded to the top shell assembly 700. As shown in FIGS. 9B-C, the assembled sensor connector 310 has a front portion 910 and a back portion 920. The front portion 910 has a socket 912 configured to removably accept a sensor plug 200 (FIGS. 5A-B). The back portion 920 is fixedly attached to a patient cable 330 (FIG. 3) electrically connecting the sensor to a monitor. Both sides of the sensor connector 310 have buttons 1610 adapted to release the sensor when pressed.

Cable Assembly Construction

Figure 10:
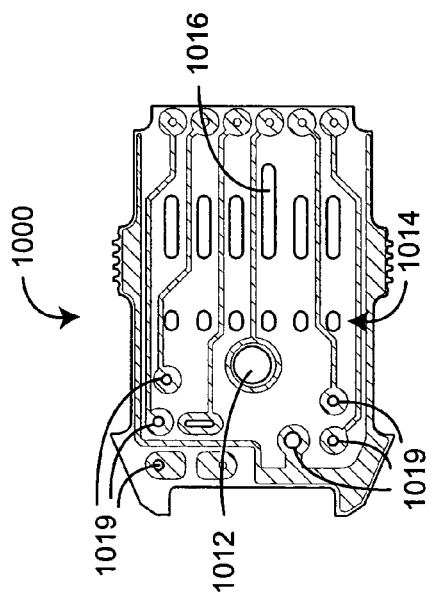
FIG. 10 is a top view of a PCB.
Figure 11A:
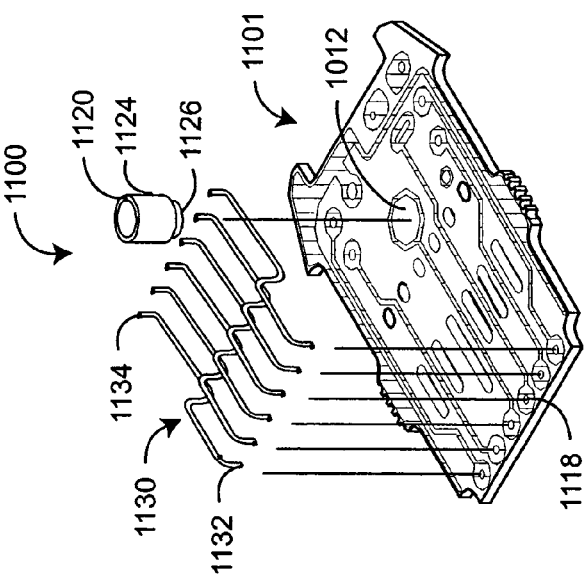
FIGS. 11A-D are exploded perspective, top, front and side views of a PCB assembly.
Figure 11C:
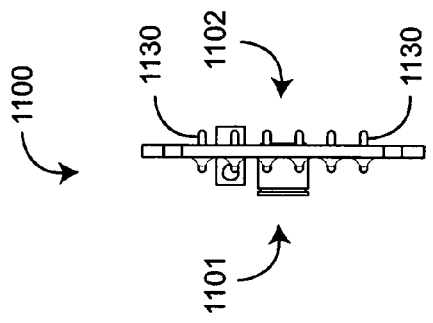
Figure 11B:
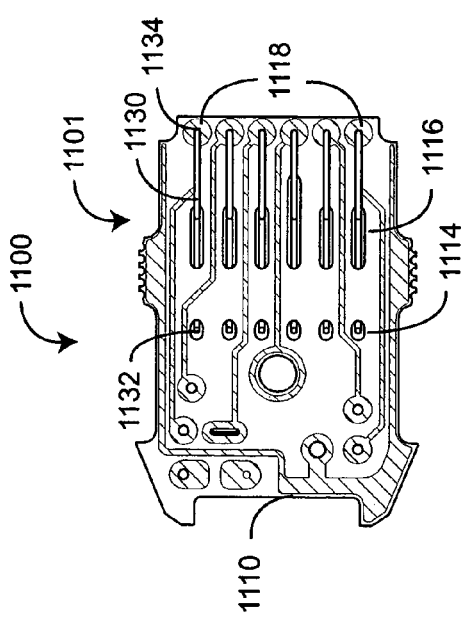
Figure 11D:
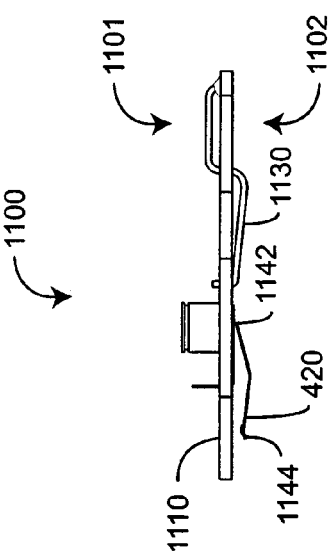
Figure 12C:
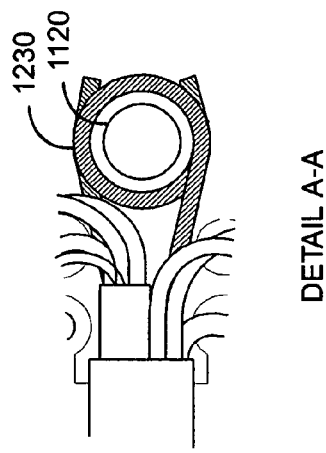
FIGS. 12A-C are top, side, and detailed top views of a wired PCB assembly.
Figure 12A:
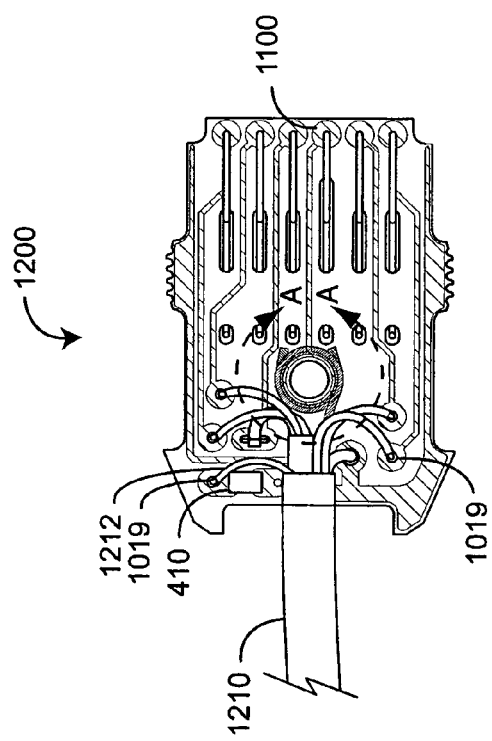
Figure 12B:
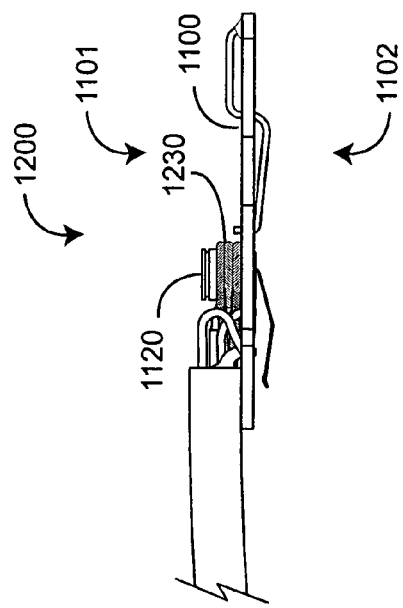
Figure 13A:
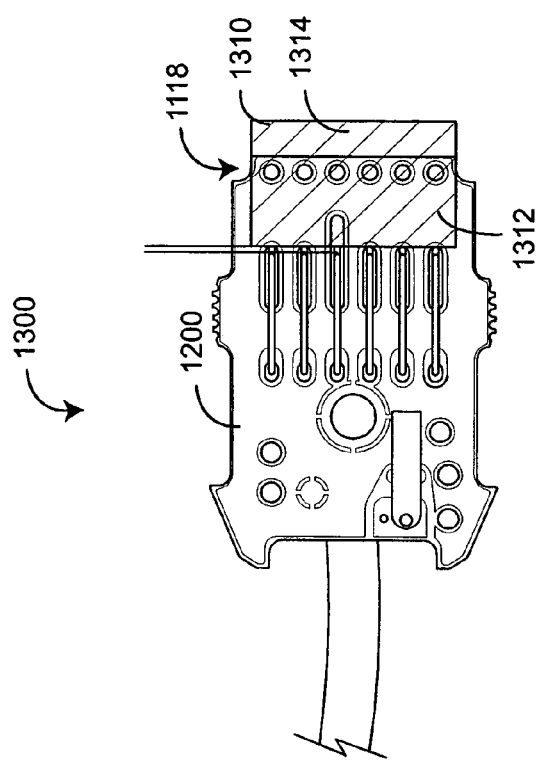
Figure 13B:
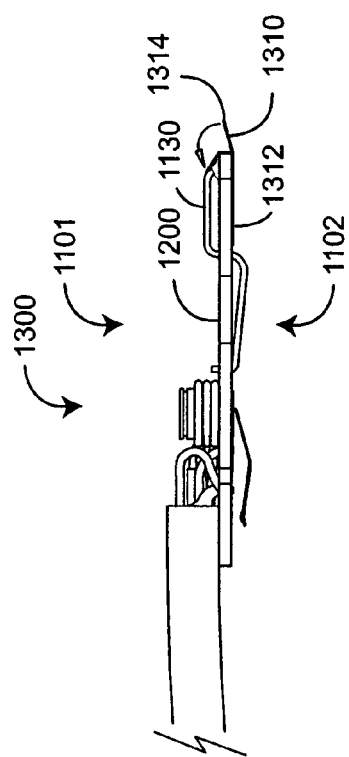

FIGS. 14A-B illustrate a cable assembly 610 having a printed circuit board (PCB) assembly 1100 (FIGS. 11A-D), an attached cable 1210 (FIGS. 12A-C) and tape 1310 (FIGS. 13A-B). As shown in FIGS. 11, the PCB assembly 1100 has a PCB 1000, a bushing 1120 and contacts 1130, a component side 1001 adapted to attach components and a plug side 1002 configured to accept a sensor plug 200 (FIGS. 5A-B). As shown in FIGS. 10-11A, the PCB 1000 has a bushing aperture 1012, end slots 1014, contact slots 1016, and pads 1019. The aperture 1012 is generally disposed off center of the PCB 1000 so as to accommodate the bushing 1120. The slots 1014, 1016 are disposed on one side of the aperture 1012 and adapted to receive the contacts 1130. The pads 1019 are distributed on the other side of the aperture 1012 and configured for a solder connection of cable wires.

Figure 1:
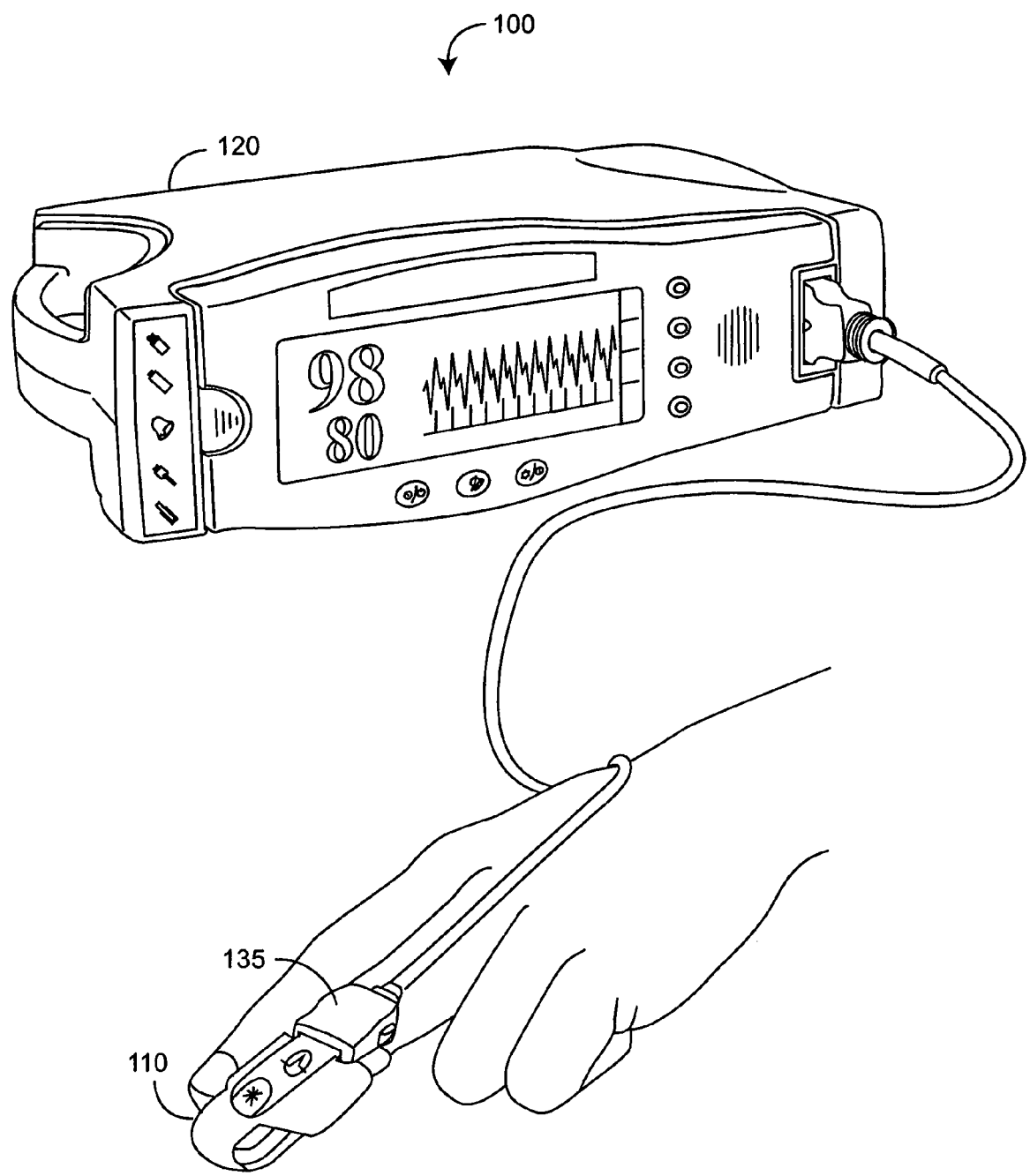
FIG. 1 is a perspective view of a pulse oximetry system.
Figure 2A:
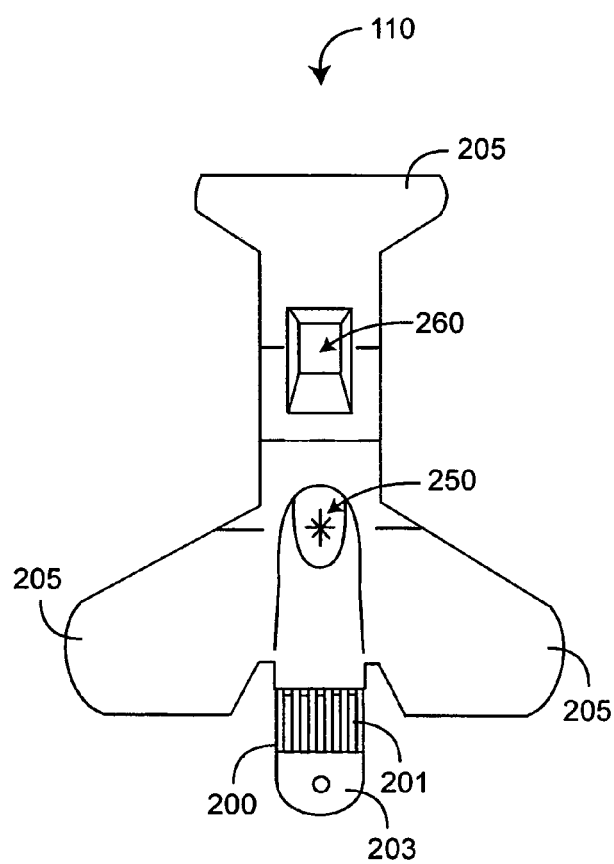
FIGS. 2A-B are a top view and a schematic diagram of a pulse oximetry sensor.
Figure 2B:
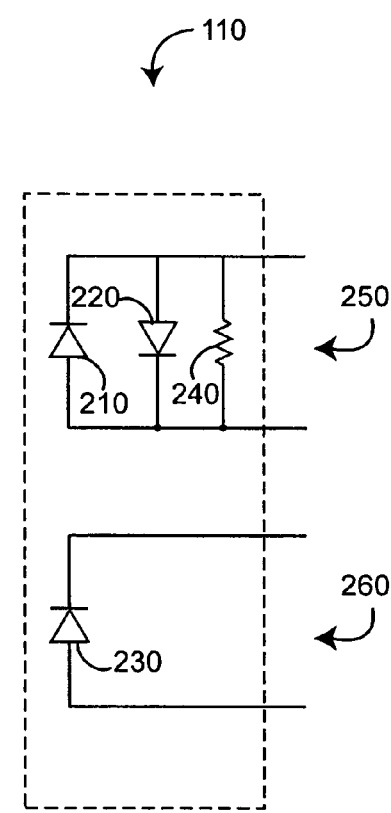

As shown in FIGS. 11A-D, the bushing 1120 is generally cylindrical having a wide portion 1124 and a narrow portion 1126. The wide portion 1124 accommodates a removable latch 1620 (FIGS. 16A-B) that is configured to secure and release a sensor plug tab 203 (FIG. 2A). The narrow portion 1126 is configured to fasten the bushing 1120 to the PCB 1000. In particular, the bushing 1120 is inserted into the PCB 1000 on the component side 1101 so that the wide portion 1124 is seated flush with the PCB 1000 surface and the narrow portion 1126 fits inside the aperture 1012.

Also shown in FIGS. 11A-D, the contacts 1130 have first ends 1132 and second ends 1134 and extend through the contact slots 1016 (FIG. 10) from the component side 1101 to the plug side 1102. The first ends 1132 are soldered into mounting holes 1118. A switch 420 mounted on the plug side 1102 has a mounted end 1142 soldered to the PCB assembly 1100 and a contact end 1144 movable between an open position 521 (FIG. 5A) and a closed position 522 (FIG. 5B), as described above.

FIGS. 12A-C illustrate a wired PCB assembly 1200 having a PCB assembly 1100, an attached cable 1210, a resistor 410 and cords 1230. Wires 1212 extend from the end of the cable 1210 and are soldered to corresponding pads 1019. Cords 1230 are wrapped around and glued to the bushing 1120. The resistor 410, described above, is attached on the component side 1101.

FIGS. 13A-B illustrate a taped PCB assembly 1300 having a wired PCB assembly 1200 and a tape 1310 which covers the soldered ends 1132 (FIG. 11A) of the contacts 1130 along the mounting pads 1118. The tape 1310 has a first portion 1312 attached over the plug side 1102 and a second portion 1314 attached over the component side 1101. In one embodiment, the tape is kapton.

FIGS. 14A-C illustrate a cable assembly 610 having a taped PCB assembly 1300 and an EMI shield 1410. The EMI shield 1410 has an aperture 1412 that accommodates the bushing 1120 and snaps into a bushing groove 1122.

Spring Assembly Construction

Figure 16:
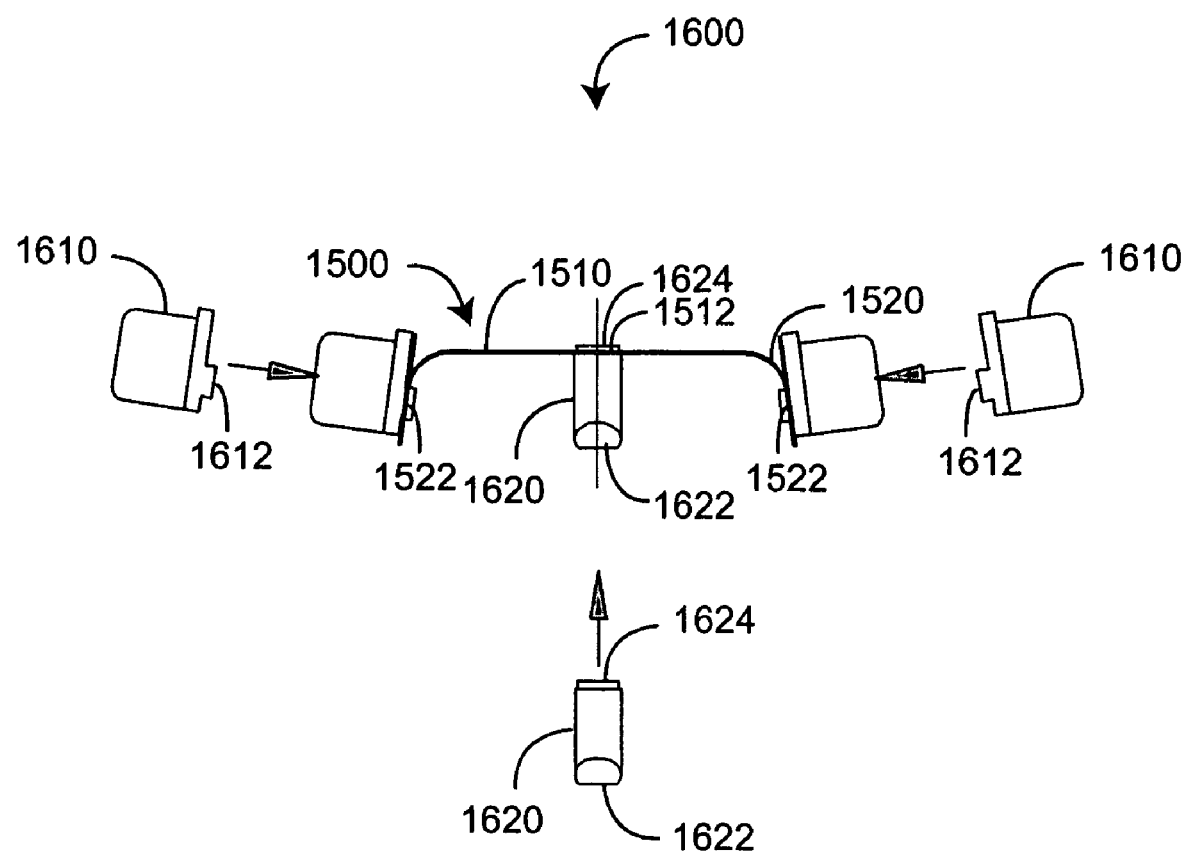
FIG. 16 is a side view of a spring and latch assembly.

FIGS. 15A-D illustrate a connector spring 1500 which actuates a latch 1620 (FIG. 10) to secure and release a sensor plug 200 (FIG. 2A). The connector spring 1500 has a spring bar 1510 and foldable sides 1520. The spring bar 1510 extends between the sides 1520 and has a centered aperture 1512 that accommodates a latch 1620 (FIG. 16). The sides 1520 have mounting holes 1522 configured to attach buttons 1610 (FIG. 16). The sides 1520 are bent so as to extend generally perpendicular to the spring bar 1510.

FIG. 16 illustrates a spring assembly 1600 having a connector spring 1500, buttons 1610 and a latch 1620. The buttons 1610 have inserts 1612 that snap into the corresponding mounting holes 1522 so as to fasten the buttons 1610 to the connector spring 1500. The latch 1620 has a inclined face 1622 and an opposite flat face 1624 and is secured into the connector spring 1500 so that the flat face 1624 fits into the aperture 1512 and is secured with the connector spring 1500. The latch 1620 is adapted to fit through the bushing 1120 (FIG. 11A). When the buttons 1610 are pressed, the sides 1520 are compressed, flexing the spring bar 1510 so as to actuate the latch 1620.

A connector switch was described above with respect to a patient cable interconnecting a disposable finger sensor and a pulse oximetry monitor. A connector switch, however, is applicable to an interconnection between any physiological sensor for attachment to various tissue sites and any corresponding monitor for measuring various physiological parameters, such as other hemoglobin species and blood glucose to name a few. Also, a connector switch was described above in terms of a switch employing a mechanical mechanism that is physically actuated to perform an electrical connection and disconnection function. Other connector switch embodiments include a switch or switches employing, for example, electrical, electromechanical, optoelectrical or electromagnetic mechanisms, to name a few, that are physically, electrically, magnetically or optically actuated to perform an electrical connection and disconnection function. Examples include, but are not limited to, transistor, optical and proximity switches and relays among others.

Further, a connector switch was described in terms of a single pole, single throw switch connecting and disconnecting a resistor between cable conductors. Other connector switch embodiments include multiple switches or multiple pole, multiple throw switches capable of selecting and deselecting or otherwise enabling and disenabling or switching between multiple information elements, including passive components, active components and various memory devices. In addition, although a connector switch was described above in terms a normally open switch, a connector switch includes a normally closed switch or switches, or a combination of normally open and normally closed switches.

A connector switch has been disclosed in detail in connection with various embodiments. These embodiments are disclosed by way of examples only and are not to limit the scope of the claims that follow. One of ordinary skill in art will appreciate many variations and modifications.

What is claimed is:

1. An interconnection between a noninvasive optical sensor and a monitor configured to receive one or more signals from said sensor indicative of light attenuated by body tissue, the monitor also configured to determine measurements for one or more physiological parameters based on the received one or more signals, the interconnection comprising:
    a cable having a plurality of conductors providing electrical communication between a sensor connector and a monitor connector;
    an information element readable by said monitor to determine information about a type of said sensor and to configure said monitor in its determination of said one or more physiological parameters based on said type, and mounted in one of said sensor connector, said monitor connector and said cable; and
    a switch mounted in said sensor connector responsive to said sensor connecting to and disconnecting from said sensor connector so as to alter the readability of said information element.

2. The interconnection according to claim 1 wherein said switch has a closed position enabling said information element to be readable by said monitor and an open position disabling said information element from being readable by said monitor.

3. The interconnection according to claim 2 wherein said switch is normally in said open position and moves from said open position to said closed position as said sensor is connected to said sensor connector.

4. The interconnection according to claim 3 wherein said information element is a resistor and said switch electrically connects said resistor between a pair of said conductors so as to enable said monitor to determine a value for said resistor.

5. An interconnection method comprising the steps of:
    providing a cable configured to communicate drive signals from a physiological parameter monitor to a noninvasive optical sensor capable of outputting a signal indicative of light attenuated by body tissue, and to communicate physiological signals from said sensor to said monitor;
    associating an information element with said cable, said information element capable of conveying information regarding said sensor to said monitor; and
    actuating a switch in response to said sensor connecting and disconnecting to said cable so as to render said information element readable and unreadable by said monitor, respectively.

6. The interconnection method according to claim 5 wherein said associating step comprises a substep of mounting said information element in a connector attached to said cable.

7. The interconnection method according to claim 6 wherein said actuating step comprising a substep of mechanically moving said switch with a portion of said sensor.

8. The interconnection method according to claim 7 wherein said actuating step comprising a substep of electrically connecting said information element to a conductor of said cable.

9. A sensor-monitor interconnection comprising:
    a cable capable of communicate signals between a physiological sensor and a physiological parameter monitor;
    an information element capable of conveying information regarding said sensor to said monitor; and
    a switch associated with said cable and responsive to said physiological sensor connecting to and disconnecting from said cable so as to enable and disable access to said information element by said monitor.

10. The sensor-monitor interconnection according to claim 9 further comprising:
    a sensor connector attached to said cable capable of electrically and mechanically connecting said sensor to said cable; and
    a monitor connector attached to said cable capable of electrically and mechanically connecting said cable to said monitor,
    wherein said information element is mounted within at least one of said sensor connector and said monitor connector.

11. The sensor-monitor interconnection according to claim 10 further comprising a plurality of conductors disposed within said cable, wherein said switch is adapted to connect and disconnect said information element to at least one of said conductors.

12. The sensor-monitor interconnection according to claim 11 further comprising a sensor portion configured to actuate said switch as said sensor is connected to said sensor connector.

* * * * *